(12) United States Patent
Otto et al.

(10) Patent No.: US 8,329,638 B2
(45) Date of Patent: Dec. 11, 2012

(54) ANTIBACTERIAL AGENT BASED ON FATTY ACID ESTERS OF HYDROXY CARBOXYLIC ACIDS

(75) Inventors: Roel Otto, Gorinchem (NL); Aldana Mariel Ramirez, Wageningen (NL); Diderik Reinder Kremer, Groningen (NL)

(73) Assignee: Purac Biochem B.V., Gorinchem (NL)

( * ) Notice: Subject to any disclaimer, the term of this patent is extended or adjusted under 35 U.S.C. 154(b) by 0 days.

(21) Appl. No.: 13/114,510

(22) Filed: May 24, 2011

(65) Prior Publication Data

US 2011/0230395 A1    Sep. 22, 2011

Related U.S. Application Data

(62) Division of application No. 12/232,424, filed on Sep. 17, 2008, now Pat. No. 7,973,006.

(60) Provisional application No. 60/960,131, filed on Sep. 17, 2007.

(51) Int. Cl.
*A61K 38/00* (2006.01)
*A61K 31/225* (2006.01)
*A01N 37/02* (2006.01)
*A01N 37/06* (2006.01)

(52) U.S. Cl. ....................... 514/1.1; 514/547

(58) Field of Classification Search .......... None
See application file for complete search history.

(56) References Cited

U.S. PATENT DOCUMENTS

| | | | |
|---|---|---|---|
| 3,275,503 A * | 9/1966 | Marnett et al. | 514/547 |
| 5,494,937 A | 2/1996 | Asgharian et al. | |
| 5,549,919 A * | 8/1996 | Ueno et al. | 426/335 |
| 7,073,006 B2 * | 7/2006 | Nguyen | 710/260 |
| 7,973,006 B2 * | 7/2011 | Otto et al. | 514/1.1 |

FOREIGN PATENT DOCUMENTS

| | | |
|---|---|---|
| EP | 0 572 271 B1 | 1/1997 |
| EP | 1 000 542 B1 | 6/2002 |
| JP | A-04-008273 | 1/1992 |
| JP | A-05-068521 | 3/1993 |
| JP | A-07-135943 | 5/1995 |
| JP | A-2000-026887 | 1/2000 |
| JP | A-2000-270821 | 10/2000 |

OTHER PUBLICATIONS

Shima et al., "Antimicrobial Action of $\epsilon$-Poly-$_L$-Lysine", *The Journal of Antibiotics*, vol. XXXVII No. 11, Jan. 19, 1984, pp. 1449-1455.
Hiraki et al., "Report of Research & Development $\epsilon$-polylysine: its Development and Utilization", *Fine Chemicals*, vol. 29, 2000, pp. 18-25.

* cited by examiner

*Primary Examiner* — Marcela M Cordero Garcia
(74) *Attorney, Agent, or Firm* — Oliff & Berridge, PLC

(57) ABSTRACT

An antibacterial composition includes a combination of fatty acid ester of fatty acid and hydroxy carboxylic acid with an antibacterial agent selected from polylysine, chitosan, protamine, their salts and mixtures hereof. The hydroxy carboxylic acid may be present as acid in its free form, in its salt form and/or in its ester form. The composition may be used as an antibacterial agent against gram-negative bacteria in various products, applications and methods.

8 Claims, 8 Drawing Sheets

ANTIBACTERIAL AGENT BASED ON FATTY ACID ESTERS OF HYDROXY CARBOXYLIC ACIDS

This is a Divisional of Application No. 12/232,424 filed Sep. 17, 2008, which in turn is a non-provisional application, that claims the benefit of U.S. Provisional Application No. 60/960,131, filed Sep. 17, 2007. The disclosures of the prior applications are hereby incorporated by reference herein in their entirety.

The present invention relates to an antibacterial composition based on fatty acid ester of hydroxy carboxylic acid and to its use as antibacterial agent against gram-negative bacteria in various products and applications. The present invention further relates to products and in particular to food products comprising said antibacterial agent.

The fatty acid esters of the present invention comprise fatty acid ester of hydroxy carboxylic acid such as for example lactic acid, citric acid, malic acid, gluconic acid and tartaric acid wherein said hydroxy carboxylic acid can also be in a salt- or ester form. Further, the hydroxy carboxylic acid may comprise one or more polymerized acid monomers, such as is the case in for example lactylates.

The majority of these fatty acid esters of hydroxy carboxylic acids are applied as emulsifier. For example, fatty acid esters of lactic acid, also referred to as lactylates and acyl lactylates, are well known for their emulsifying effect. They are commonly applied in the bakery industry.

Some of the lactylates of interest are described in U.S. Pat. No. 3,275,503 and EP 0572271 and are represented with the general formula:

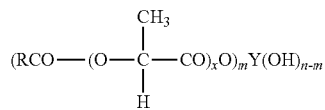

wherein RCO is an acyl radical of a fatty acid with 4 to 12 carbon atoms, Y is a cation selected from hydrogen, alkali metal, alkaline earth metal, zinc, silver, ammonium or substituted ammonium having one or more C1-C3 alkyl or hydroxy alkyl groups; n represents the value of the cation and m is an integer of from 1 to n, x is a number of from 1 to 6 and preferably 1 to 3.

The lactylates described in U.S. Pat. No. 3,275,503 have an acyl group RCO with 8 to 12 carbon atoms and are described to inhibit the growth of mildew and mold development by yeasts and fungi originating from e.g. Rhizopus, Penicillum, *Aspergillus, Trichophyton*, and *Saccaromyces*. The lactylates in question also show some antibacterial activity against *Staphylococcus aureus* and *Bacillus mesentericus*, which are both gram-positive bacteria.

The lactylates described in EP 0572271 have an acyl group RCO with 4 to 7 carbon atoms and have some antibacterial activity against *Pseudomonas cepacia*, which is a gram-negative bacterium.

Lactylates, and more in particular lactylates of the above formula having an acyl group RCO with 8 to 12 carbon atoms, are however not known to be very effective against gram-negative bacteria such as e.g. *Escherichia coli, Salmonella* and *Campylobacter*. They are therefore also not used as antibacterial agents. In fact, their regulatory status is that of them being used as emulsifying agent only.

The same applies to fatty acid esters of other hydroxy carboxylic acids such as for example the fatty acid esters of citric acid, malic acid and tartaric acid. These esters are mainly used as emulsifiers in various types of products and not for antibacterial purposes.

The present invention provides a solution to overcome above-mentioned lack in efficiency against gram-negative bacteria. The present invention provides a means to render the group of fatty acid esters of hydroxy carboxylic acids as described above significantly more active against gram-negative bacteria, thereby making them very useful as antibacterial agents for application in a wide variety of food, drink and other products such as e.g. in feed applications, in detergents and cosmetic products.

Hereto, the present invention is directed to an antibacterial composition comprising a combination of fatty acid ester of fatty acid and hydroxy carboxylic acid and/or the salt and/or ester of said hydroxy carboxylic acid with one or more antibacterial agents selected from polylysine, chitosan, protamine and their salts.

It is found that the above-mentioned antibacterial agents not simply enhance the activity of fatty acid esters of hydroxy carboxylic acids whereby said enhancing effect is the sum of the individual activities of the fatty acid ester and the antibacterial agent, but the antibacterial agent and the fatty acid ester of the present invention work in synergy resulting in an antibacterial activity which is significantly higher than the sum of the activities of the individual components of the antibacterial composition.

Polylysine is known to exert an antibacterial activity against gram-negative bacteria. Both α-polylysine and ε-polylysine have antibacterial activity although the latter one in significant greater extent as described by Shima et al. (November 1984). The article describes that ε-polylysine can effectively be used against gram-positive and -negative bacteria such as for example *Escherichia coli* in concentrations of about 1~8 microgram per ml.

Hiraki et al. (2000) describe combinations of ε-polylysine with antibacterial agents such as glycine, acetic acid/vinegar, ethanol or thiamine laurylsulfonate. No mention is however made of a composition wherein polylysine is combined with fatty acid ester of hydroxy carboxylic acid effective as antibacterial agent against gram-negative bacteria.

JP 2000-270821, JP 7-135943, JP 4-8273 describe compositions comprising ε-polylysine in combination with glycerol fatty acid esters, protamines, ethanol, glycine and/or hydroxy carboxylic acids and their salts. Above-mentioned compositions are described to be effective against yeasts and fungi and against putrefactive or food-spoilage bacteria such as *Candida* and Luconostoc. The specific combination of polylysine and/or salts hereof with fatty acid ester of hydroxy carboxylic acid is not disclosed.

Protamine is also a commonly applied antibacterial agent. Many Japanese patent applications describe antibacterial compositions comprising combinations of protamine with various other antibacterial components such as for example glycerides, hydroxy carboxylic acids and/or their salts, amino acids, polylysine, ethanol, etceteras. No mention is made however of the specific combination of protamine and/or salts hereof with fatty acid ester of hydroxy carboxylic acid.

The same is valid for chitosan, which is an antibacterial polysaccharide and which has been applied in various combinations except with the fatty acid esters of hydroxy carboxylic acid of the present invention.

The above-mentioned combinations of fatty acid ester of fatty acid and hydroxy carboxylic acid and/or its salt with polylysine, protamine, chitosan in their free form and/or in their salt form and/or any combination hereof have thus not been described before. Neither has the synergistic antibacterial activity of said combination against gram-negative bacteria been acknowledged before.

The fatty acid ester of the present invention is an ester of fatty acid and hydroxy carboxylic acid and/or a salt hereof. As the person skilled in the art knows, such an ester may be obtained via for example an esterification or enzymatic process. As is common knowledge, most processes for the manufacture of fatty acid esters result in a mixture of fatty acid esters whereby said mixture is for example a mixture of fatty acid esters of different fatty acid tails or of different ester tails. A specific fatty acid in its pure form may be obtained out of this mixture by various means that are well known to the person skilled in the art.

The fatty acid reactant may be a saturated or unsaturated fatty acid comprising 4 to 18 and preferably 8 to 18 carbon atoms. Non-limiting examples hereof are butyric acid (i.e. butanoic acid (C4)), caproic acid (i.e. hexanoic (C6)), myristic acid (i.e. tetradecanoic acid (C14)), stearic acid (i.e. octadecanoic acid (C18)), myristoleic acid (C14) and/or oleic acid (C18).

The hydroxy carboxylic acid may comprise one monomer of hydroxy carboxylic acid or several monomers of hydroxy carboxylic acid linked to each other by polymerized bonds. Said monomer of hydroxy carboxylic acid may comprise 1 to 6 carbon atoms such as for example the monomer of lactic acid, malic acid, citric acid, gluconic and tartaric acid. Further, the salts and/or esters of said hydroxy carboxylic acid are also very suitable for the antibacterial composition according to the present invention.

In a preferred embodiment of the present invention, the antibacterial composition comprises fatty acid ester of lactic acid and/or the salt of lactic acid, also referred to as lactylates.

The lactylates of the present invention have the following formula:

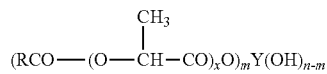

wherein RCO is an acyl radical of a fatty acid with 4 to 18 carbon atoms, and preferably 8 to 18 carbon atoms, Y is a cation selected from hydrogen, alkali metal, alkaline earth metal, zinc, iron, ammonium and substituted ammonium having one or more C1-C3 alkyl or hydroxy alkyl groups; n represents the value of the cation and m is an integer of from 1 to n; x represents the number of monomer units and has a value of from 1 to 6 and preferably of from 1 to 3.

Components wherein x is for example 1 are referred to as monolactylates and wherein x is 2 are called dilactylates. The lactylate components are often obtained as mixtures of for example a mixture of predominantly monolactylates and further comprising dilactylates due to the way in which they are prepared. It may be very well possible that also higher polymerized lactylates are present in the mixture. The parameters x, m and n as described above thus present average numbers.

The lactylates may be obtained in their pure form (e.g. only the mono-form) by means of for example chromatographic separation or by any other means known to the person skilled in the art.

Good results were obtained with mixtures predominantly containing mono-and/or di-lactylate esters of octanoic acid (C8), or decanoic acid (C10), or dodecanoic acid (C12) or tetradecanoic acid (C14), or palmitic acid (C16), or oleic acid (C18:1) and the sodium, potassium and calcium salts hereof.

Instead of lactylates, it has been observed that the esters of lactic acid may also be used to form fatty acid esters with.

Thus, the fatty acid ester of a fatty acid such as for example octanoic acid or dodecanoic acid with a lactate ester such as for example ethyl-lactate works well in combination with one or more antibacterial agents such as polylysine, protamine and chitosan and/or salts hereof.

Polylysine may be present as ε-polylysine, as α-polylysine or as a mixture hereof. ε-Polylysine is preferred as it has a higher antibacterial activity against gram-negative bacteria than the other forms of polylysine and thus lesser amounts of this antibacterial agent are needed in the applications. ε-Polylysine is a homopolymer containing 25-35 L-lysine residues. The systematic name of ε-polylysine is poly(imino (2-amino-1-oxo-1,6-hexanediyl)). The empirical formula for the typical ε-polylysine homopolymer is $C_{180}H_{362}N_{60}O_{31}$ with a molecular weight of approximately 4700 (30 L-lysine residues). The chemical Abstract Service (CAS) number for ε-polylysine is 28211-04-3. The fatty acid esters of the present invention may also be combined with one or more salts of polylysine. Examples hereof is the salt of an inorganic acid such as hydrochloric acid, sulfuric acid, phosphoric acid etceteras or of an organic acid such as lactic acid, acetic acid, propionic acid, fumaric acid, malic acid, citric acid etceteras. Although there is no substantial difference in antibacterial effect, polylysine is sometimes preferably used in the free form because of limited solubility of the polylysine in salt form.

The protamine, a small arginine-rich protein, may also be used in its free form and in the form of a salt. Suitable protamine is for example protamine sulfate or protamine hydrochloride.

Chitosan is a β-1,4-linked polymer of glucosamine and lesser amounts of N-acetylglucosamine. It is not a single compound but a group of partially deacetylated products with varying chain lengths. As the person skilled in the art knows, chitosan is more effective against gram-negative bacteria at a pH below 6.3 as chitosan becomes more positively charged and is better soluble. Highly deacetylated chitosans have a similar effect. The chain length of this polymeric compound and the molecular weight also have effect on the degree of antibacterial activity. It was found that chitosan with a molecular weight of between 1 and 2000 kDalton shows a satisfactory antibacterial activity. Preferred is chitosan of a molecular weight of between 300-2000 and 300-1000 as it shows a higher efficacy. Chitosan may be used in its free form and in its salt form. Suited salts are for example chitosan as acetic acid or lactic acid salt or as glutamic acid salt.

Optionally, said antibacterial composition further comprises one or more metal chelating agents. The chelating agent may be selected from for example ethylene diamine tetraacetic acid (EDTA) and salts thereof, diethylenetri-aminepenta-acetic acid and salts thereof, various phosphate-based compounds such as sodium hexametaphosphate, sodium acid pyrophosphate and polyphosphoric acid, orga-nophosphonate chelating compounds such as: phytic acid, 1,1-diphosphonic acid, siderophores and iron binding proteins such as enterobacterin and lactoferrin, and hydroxy carboxylic acids and/or salts thereof such as for example and not limited to succinic acid, ascorbic acid, glycolic acid, benzoic acid, sorbic acid, octanoic acid, adipic acid.

The antibacterial composition of the present invention may preferably comprise one or more organic acids and/or their salts or esters selected from lactic acid, acetic acid, citric acid, malic acid, fumaric acid, tartaric acid, gluconic acid, propionic acid, caproic acid and phytic acid as these acids further enhance the antibacterial activity while not negatively affecting the quality of the products in which they are applied in terms of for example taste, texture, color and odor.

In a further preferred embodiment, the antibacterial composition of the present invention further comprises a glycerol-based fatty acid ester. Said glycerol fatty acid ester, also referred to as glyceride, may comprise a monoester, a di-ester or a tri-ester of glycerol or mixtures hereof. Said glycerides have been observed to further increase the antibacterial effect against gram-negative bacteria.

The present invention further relates to the use of an antibacterial composition of the present invention as antibacterial agent against gram-negative bacteria. It is found that the antibacterial compositions of the present invention in particular show a very high (synergistic) activity against *Escherichia coli*, *Salmonella* spp, *Pseudomonas* spp and *Campylobacter* spp.

The various described antibacterial compositions of the present invention are applicable in a great variety of products and applications, ranging from for example products of low and high pH-values, highly concentrated and diluted products, products usable in the technical field (e.g. in detergents for industrial or house-hold use), in the pharmaceutical field (e.g. for cleaning/disinfection of equipment or in the preparation of pharmaceutical compositions or their packaging), in personal care (e.g. in manufacture of cosmetics, shampoos, creams and lotions), in the feed industry (e.g. for cleaning of equipment, in the manufacture, storage, handling and preparation of animal feed and drink products) and in the food and drink industry.

The antibacterial composition of the present invention is especially very suited for reducing and/or preventing the presence, the growth and/or activity of any gram-negative bacteria cells in the manufacture, handling, application, storage and preparation of food and drink products.

It is very suitable for application in food and drink products such as beverages (e.g. carbonated soft drinks, fruit/vegetable-based juices), high protein-containing products such as meat and fish products, dressings and toppings, ready-to-eat and ready-to-drink products, refrigerated and high temperature-treated products etceteras.

When applied in the food or drink product, the fatty acid ester of the present invention such as e.g. a lactylate will normally be present in said product in an amount of up to 1% by weight of the product, preferably from 0.0001% to 1%, or even from 0.0001% to 0.1% and most preferably from 0.0001% to 0.01%.

Polylysine, protamine and chitosan may be present in a food or drink product in an amount of up to 1% by weight of the product, preferably from 0.0001% to 1% or even from 0.0001% to 0.1%, more preferably from 0.0001% to 0.01% and most preferably from 0.0001% to 0.001%.

EDTA, organophosphates and polyphosphates will normally be present in a food or drink product in an amount of up to 1% by weight of the product, preferably from 0.0001% to 1%.

Organic acids such as for example lactic acid, fumaric acid, succinic acid, tartaric acid, ascorbic acid, glycolic acid, benzoic acid, acetic acid, propionic acid, octanoic acid, malic acid and adipic acid may be present in a food or drink product in an amount of up to 10% by weight of the product, preferably from 0.0001% to 10%, preferably from 0.0001% to 5%.

In above-mentioned applications, the antibacterial composition of the present invention is present as ingredient in the final food or drink product.

The antibacterial composition may be present on the surface of said products or inside the products. The present invention is related to a method for reducing or preventing the presence, growth or activity of gram-negative bacteria in a food or drink product wherein said method comprises contacting said food or drink product during one or more of the various stages in the food processing process including the stages of the manufacture, the handling, the storage and/or the preparation of said food or drink product. It may be applied not only in the final product stage but also during or in for example the disinfection of carcasses in the manufacture of meat products or in the washing step applied for fruit and vegetables. The antibacterial composition may be applied or introduced by various means such as for example as a spray, a rinse or a wash solution or as solution wherein the various food products are dipped. The antibacterial composition of the present invention may also be introduced by injection into the food and/or drink product.

Dependent on the type of application and on whether the antibacterial composition of the present invention is used as active ingredient in the final product or as component of for example a wash solution, the components of the antibacterial composition will vary in concentration and in internal ratio as will be obvious to the person skilled in the art.

The antibacterial composition may be available in solid or liquid form. If the antibacterial composition is in liquid form, it generally is in the form of an aqueous composition, which may be a solution or a dispersion. Such aqueous antibacterial composition according to the present invention generally comprises, based on total weight of the solution, from 0.0001 wt % to up to 40 wt %, more preferably from 0.1 wt % to 35 wt %, and most preferably from 1 to 25 wt % of an antibacterial agent of the present invention such as e.g. polylysine and from 0.0001 wt % up to 45wt. %, more preferably from 1 to 40 wt %, and most preferably from 5 to 35 wt % of fatty acid ester according to the present invention such as e.g. lactylate. The antibacterial composition may further comprise a glyceride in an amount of 0 to 45 wt % and more preferably from 0 to 35 wt % and further an organic acid in the range of 0 to 45 wt % and more preferably from 0 to 30 wt %.

The components of the antibacterial composition according to the present invention may be introduced in the liquid antibacterial composition by means of carriers. The person skilled in the art knows what type of carriers can be used. Among various well-known carriers, it was found that polyethylene glycol and/or lactate function very well as carrier. The carrier may be present in concentrations of about 50 to 98 wt %. Further, various emulsifiers known to the person skilled in the art may be added. Preferably emulsifiers such as polysorbates (e.g. polysorbate 60 or 80) and lecithine are applied in concentrations of for example 0.1 to 25%, more preferably 1-10% and most preferably 2 to 4% based on 100% fatty acid derivative, such as glyceride and/or lactylate.

If the antibacterial composition is in solid form, it will generally be in the form of a powder comprising particles of the relevant components. The antibacterial composition in solid form generally comprises, based on total weight of the powder, from 0.0001 wt % to up to 40 wt %, more preferably from 0.1 wt % to 35 wt %, and most preferably from 1 to 25 wt % of an antibacterial agent of the present invention such as e.g. polylysine and from 0.0001 wt % up to 45wt. %, more preferably from 1 to 40 wt %, and most preferably from 5 to 35 wt % of fatty acid ester derivative according to the present invention such as e.g. lactylate.

Use may be made of carriers. Very suitable carriers are silica and/or maltodextrine, which are present in concentrations up to 50 to 98 wt %.

The antibacterial composition may further comprise a glyceride in an amount of 0 to 45 wt % and more preferably from 0 to 35 wt % and further an organic acid in the range of 0 to 45 wt % and more preferably from 0 to 30 wt %.

The following non-limiting examples further illustrate the invention.

EXAMPLES

The following cultures were used in a study: *Escherichia coli* serotype O157:H7 (ATCC 700728), *Salmonella typhimurium* (ATCC 13311) and *Salmonella entiritidis* (ATCC 13076). All cultures were transferred daily in screw-capped tubes containing 10 ml brain heart infusion broth. Cultures were incubated at 30° C. without agitation. Brain heart infusion broth was prepared with increasing amounts of lactylate and polylysine. The concentration range for the caprylic (C8) lactylate was as from 0 to 0.45% in 10 0.05% steps, for the capric (C10) lactylate was as from 0 to 0.09% in 10 0.01% steps, for the lauric (C12) lactylate was as from 0 to 0.009% in 10 0.001% steps and for the tetradecanoic (C14) lactylate was as from 0 to 0.009% in 10 0.001% steps. Lactylates were combined with polylysine. The concentration range for the polylysine was as from 0 to 0.0675% in 10 0.0075% steps. This resulted in 100 different media. The pH of the media was adjusted to 6.1-6.2 with 1 N HCl or 1 N NaOH. Media were prepared in 10 ml quantities and sterilized by filtration. 300 μl of each medium was transferred to a panel of a sterile Bioscreen® honeycomb 100 well plate. Well plates were inoculated with 5 μl of a culture that was grown overnight in brain heart infusion broth using a sterile 5 μl repeating dispenser. Growth rates were determined with a Bioscreen® C that kinetically measures the development of turbidity by vertical photometry. The plates were incubated for 16-24 hours at 37° C., the optical density of the cultures was measured every 30 minutes at 420-580 nm using a wide band filter. The Bioscreen® measures at set time intervals the optical density of the cultures. From these data the Bioscreen® calculates maximum specific growth rates. The purpose of further data processing is to ascertain whether two amino acids act independently of each other or whether they stimulate each other in their inhibitory action (synergy) or cancel out each other inhibitory effect (antagonism). When a certain compound has no effect on an organism the specific growth rate of this organism (p) can be expressed as a function ($f$) of the growth limiting substrate concentration (s) by for example the Monod equation, which reads: $\mu = \mu_{max} \cdot s / (K_s + s)$, where $\mu_{max}$ represents the maximum specific growth rate, s the standing concentration of the growth limiting substrate in the medium and $K_s$ the substrate concentration where $\mu = 0.5\ \mu_{max}$. However, when the presence of an inhibitor P affects cell growth the function $f$ for $\mu$ must be modified i.e. $\mu = f(s,p)$, where p represents the concentration of inhibitor P. Numerous studies of growth inhibition kinetics of bacteria have shown that many inhibitors behave as non-competitive inhibitors. This implies that only the maximum specific growth rate ($\mu_{max}$) value and not the affinity ($K_s$) is affected. Therefore the specific growth rate in the presence of inhibitor can be written as: $\mu = \mu_i \cdot s / (K_s + s)$, where $\mu_i$ is the maximal specific growth rate in the presence of a inhibitor P. The relationship between $\mu_i$ and $\mu_{max}$ and the concentration of the inhibitor P was describes using the Logistic Dose Response equation, which reads: $\mu_i / \mu_{max} = 1 / (1 + (p/p_{0.5})^b)$ (Jungbauer, A. (2001). The logistic dose response function: a robust fitting function for transition phenomena in life sciences. J. Clinical Ligand Assay 24: 270-274). In this equation p represents the concentration of inhibitor P and $p_{0.5}$ the concentration of P where $\mu_i = 0.5\ \mu_{max}$; $\mu_{max}$ is the maximum specific growth rate that is the specific growth rate in the absence of inhibitor P, b is a dimensionless quantity, which determines the relationship between $\mu_i$ and p. Combining the Monod and Logistic Dose Response equation it can be written as: $\mu = \mu_{max}(s/K_s+s)/(1+(p/p_{0.5})^b)$. In batch culture where s is usually many times higher than $K_s$ this equation reduces to $\mu = \mu_{max}/(1+(p/p_{0.5})^b)$. When comparing different organisms grown under the same conditions, or the same organism grown under different conditions, it is more meaningful to use relative growth rate, rather than absolute growth rates as standards of comparison. Relative growth rate (O) is the ratio of growth rate ($\mu$) to maximum growth rate ($\mu_{max}$) i.e. $O = \mu/\mu_{max}$. It can be seen that while $\mu$ and $\mu_{max}$ have the dimensions of (time)$^{-1}$, their ratio O is dimensionless, i.e. a pure number. Similarly we can define the relative inhibitor concentration $\epsilon$ as $p/p_{0.5}$. The reduced Monod and Logistic Dose Response equation can now be written as: $O = 1/(1+\epsilon^b)$. For two inhibitors X and Y e.g. the following two expressions for O can be defined: $O_x = 1/(1+\epsilon^{b2})$ and $O_y = 1/(1+\epsilon^{b2})$. $O_x$ and $O_y$ can be experimentally evaluated by examining the inhibitory effects of either X or Y on the growth rate of the target organism. Knowing the evaluated functions for $O_x$ and $O_y$ the theoretical independent effect is defined as: $O_x \cdot O_y$. The experimentally observed effect of combinations of X and Y on the relative growth rate is defined as $O_{xy}$. The hypothesis that X and Y act independently of each other on a certain organism mathematically translates to $O_{xy}/O_x \cdot O_y = 1$. Rejection of this hypothesis implies that the combined effect of X and Y is not an independent effect but either synergistic or antagonistic. In case the inhibitors X and Y act synergistically upon the target organism $O_{xy}/O_x \cdot O_y < 1$ (but $>0$). In those cases that the combined effect of inhibitors X and Y is antagonistic $O_{xy}/O_x \cdot O_y > 1$.

Synergy, independent effect, and antagonism can be visualized in a plot of $O_{xy}$ versus $O_x \cdot O_y$. This is exemplified in FIGS. 1-8, wherein different plots are given of $O_{CxL.pLys}$) experimentally observed relative growth rate in the presence of mixtures of a lactylate and polylysine) versus $O_{CxL} \cdot O_{pLys}$ (predicted relative growth rate in the presence of mixtures of a lactylate and polylysine) for *Salmonella typhimurium* (ATCC 13311) and *Salmonella entiritidis* (ATCC 13076) showing the synergy in inhibition between lactylates and polylysine. The solid line in these graphs represents the line where the experimentally observed relative growth rate ($O_{CxL.pLys}$) equals the predicted relative growth rate ($O_{CxL} \cdot O_{pLys}$) and where the lactylate and polylysine act as independent inhibitors.

Figure 1:
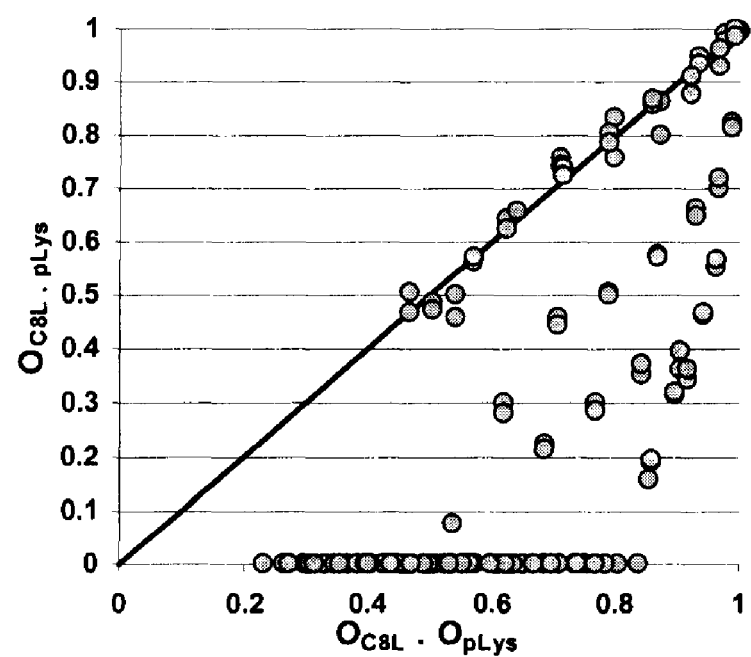
FIG. 1 represents a plot of experimentally observed relative growth rate of *Salmonella typhimurium* in the presence of mixtures of a C8-lactylate and polylysine ($O_{C8L.pLys}$) versus predicted relative growth rate in the presence of mixtures of C8-lactylate and polylysine ($O_{CxL} \cdot O_{pLys}$).
Figure 2:
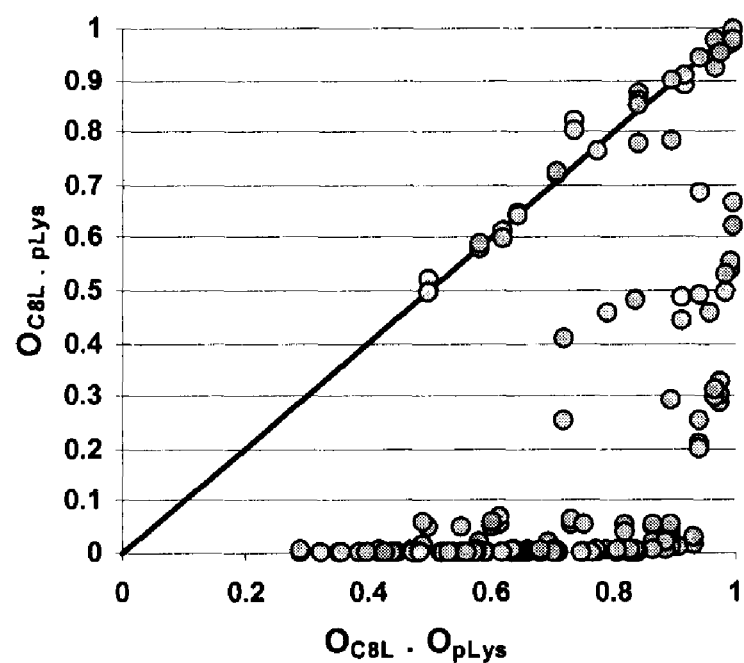
FIG. 2 represents a plot of experimentally observed relative growth rate of *Salmonella entiritidis* in the presence of mixtures of a C8-lactylate and polylysine ($O_{C8L.pLys}$) versus predicted relative growth rate in the presence of mixtures of C8-lactylate and polylysine ($O_{C8L} \cdot O_{pLys}$).
Figure 3:
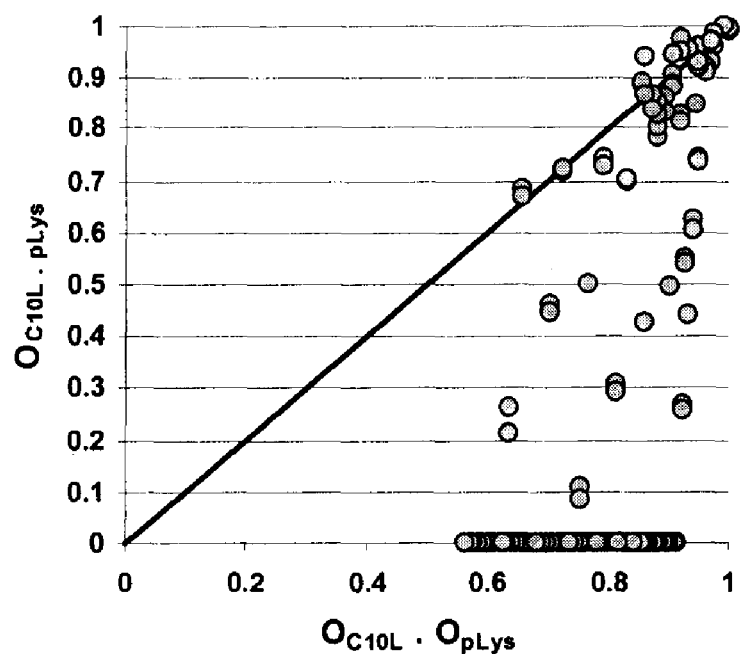
FIG. 3 represents a plot of experimentally observed relative growth rate of *Salmonella typhimurium* in the presence of mixtures of a C10-lactylate and polylysine ($O_{C10L.pLys}$) versus predicted relative growth rate in the presence of mixtures of C10-lactylate and polylysine ($O_{C10L} \cdot O_{pLys}$).
Figure 4:
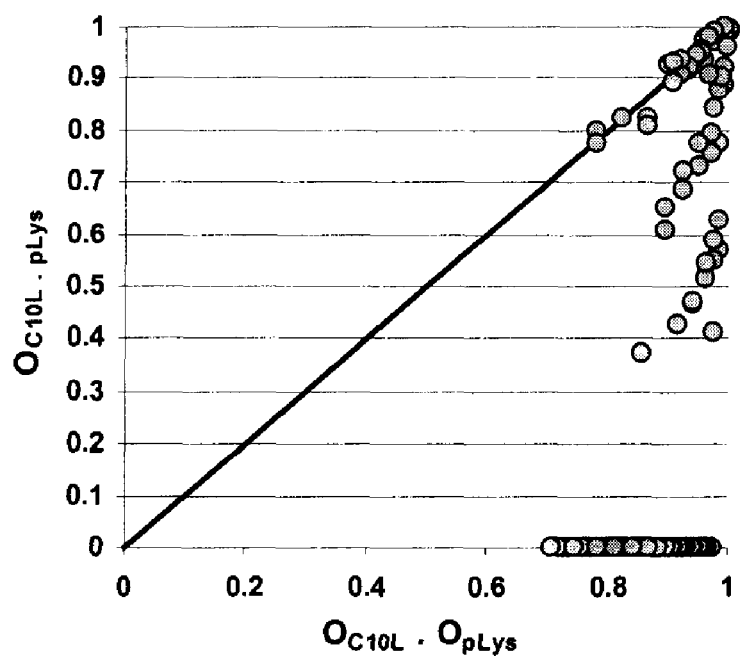
FIG. 4 represents a plot of experimentally observed relative growth rate of *Salmonella entiritidis* in the presence of mixtures of a C10-lactylate and polylysine ($O_{C10L.pLys}$) versus predicted relative growth rate in the presence of mixtures of C10-lactylate and polylysine ($O_{C10L} \cdot O_{pLys}$).
Figure 5:
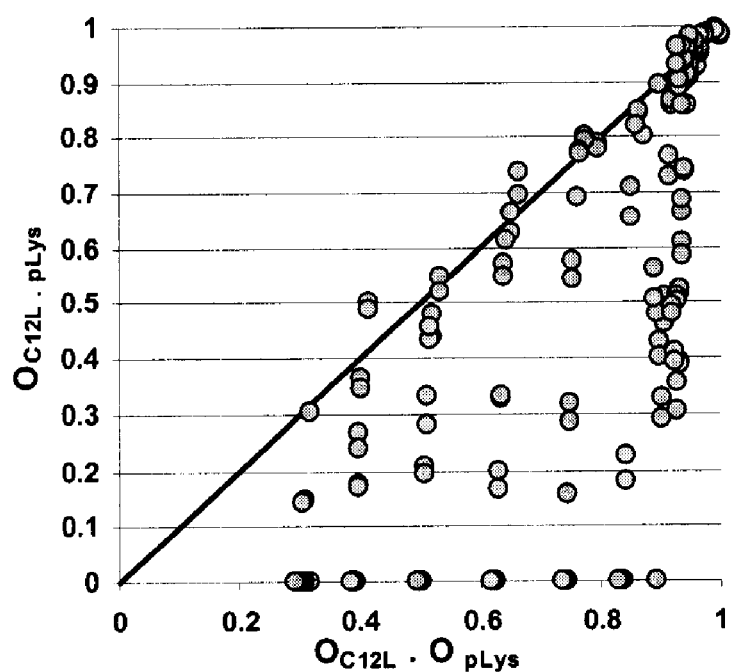
FIG. 5 represents a plot of experimentally observed relative growth rate of *Salmonella typhimurium* in the presence of mixtures of a C12-lactylate and polylysine ($O_{C12L.pLys}$) versus predicted relative growth rate in the presence of mixtures of C12-lactylate and polylysine ($O_{C12L}·O_{pLys}$).
Figure 6:
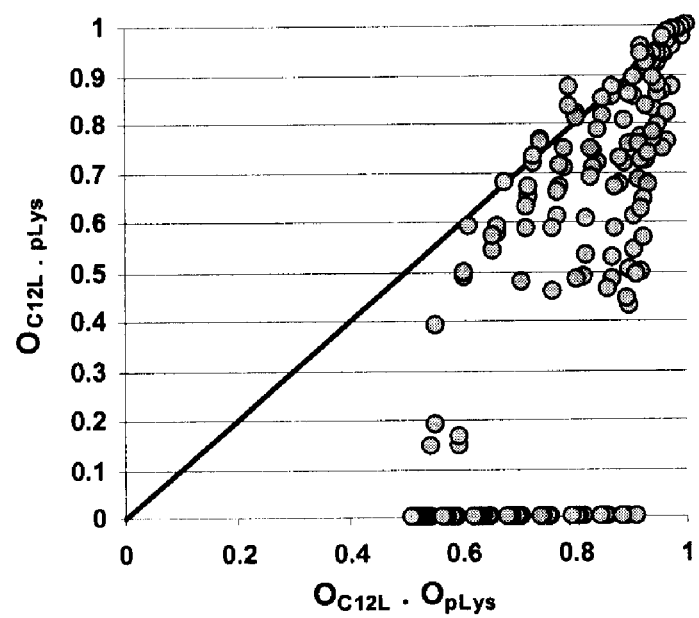
FIG. 6 represents a plot of experimentally observed relative growth rate of *Salmonella entiritidis* in the presence of mixtures of a C12-lactylate and polylysine ($O_{C12L.pLys}$) versus predicted relative growth rate in the presence of mixtures of C12-lactylate and polylysine ($O_{C12L}·O_{pLys}$).
Figure 7:
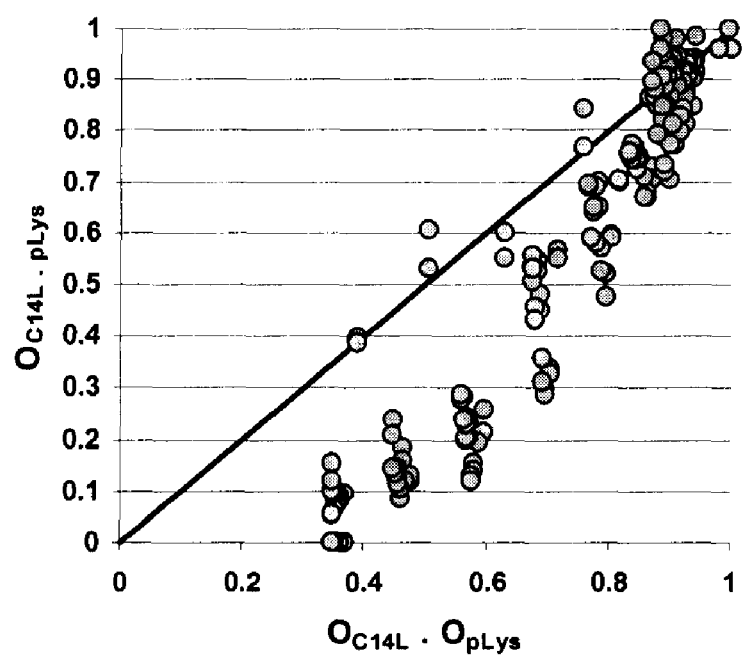
FIG. 7 represents a plot of experimentally observed relative growth rate of *Salmonella typhiinurium* in the presence of mixtures of a C14-lactylate and polylysine ($O_{C14L.pLys}$) versus predicted relative growth rate in the presence of mixtures of C14-lactylate and polylysine ($O_{C12L}·O_{pLys}$).
Figure 8:
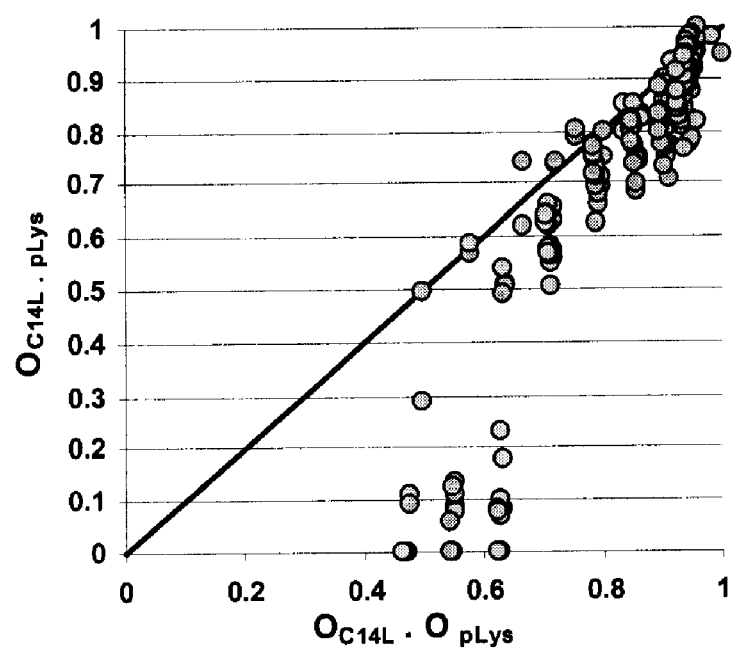
FIG. 8 represents a plot of experimentally observed relative growth rate of *Salmonella entiritidis* in the presence of mixtures of a C12-lactylate and polylysine ($O_{C12L.pLys}$) versus predicted relative growth rate in the presence of mixtures of C12-lactylate and polylysine ($O_{C12L}·O_{pLys}$).

FIGS. 1-8 demonstrate that polylysine and lactylates in the various combinations tested act synergistically upon the target organism as $O_{xy}/O_x·O_y<1$ and $>0$ (represented by the dots below the solid line).

Further examples of synergy are given in Table 1 such as for example the synergy between 0.0225% (w/w) polylysine and 0.45% (w/w) C8-lactylate or 0.0225% (w/w) polylysine and 0.09%(w/w) C10-lactylate or 0.0225% (w/w) polylysine and 0.009% C12-lactylate or 0.0225% (w/w) polylysine and 0.009% C14-lactylate.

As can be observed in the Table, the relative growth rate of Escherichia coli (ATCC 8739), *Escherichia coli* serotype 0157:H7 (ATCC 700728), *Salmonella typhimurium* (ATCC 13311) or *Salmonella entiritidis* (ATCC 13076) in a broth containing 0.0225% (w/w) polylysine and 0.45% (w/w) C8-lactylate or 0.0225% (w/w) polylysine and 0.09%(w/w) C10-lactylate or 0.0225% (w/w) polylysine and 0.009% C12-lactylate or 0.0225% (w/w) polylysine and 0.009% C14-lactylate is lower than can be expected on the basis of the relative growth rate of these organisms in media containing either polylysine or one of the lactylate esters.

TABLE 1

Examples of synergy

| Compound Concentration (w/w) | Observed Relative Growth Rate | | |
|---|---|---|---|
| | C8-lactylate 0.45% | polylysine 0.0225% | C8-lactylate plus polylysine 0.45%/0.0225% |
| *Escherichia coli* ATCC 8739 | 0.5625 | 0.68 | 0.0000 |
| *E. coli* O157:H7 ATCC 700728 | 0.657 | 0.838 | 0.0403 |
| *Salmonella typhimurium* ATCC 13311 | 0.47625 | 0.943 | 0.0000 |
| *S. enteritidis* ATCC 13076 | 0.58 | 0.9645 | 0.0000 |

| Compound Concentration (w/w) | Observed Relative Growth Rate | | |
|---|---|---|---|
| | C10-lactylate 0.09% | polylysine 0.0225% | C10-lactylate plus polylysine 0.09%/0.0225% |
| *Escherichia coli* ATCC 8739 | 0.721 | 0.4935 | 0.0171 |
| *E. coli* O157:H7 ATCC 700728 | 0.766 | 0.489 | 0.0000 |
| *Salmonella typhimurium* ATCC 13311 | 0.904 | 0.9725 | 0.0000 |
| *S. enteritidis* ATCC 13076 | 0.912 | 0.971 | 0.0000 |

| Compound Concentration (w/) | Observed Relative Growth Rate | | |
|---|---|---|---|
| | C12-lactylate 0.009% | polylysine 0.0225% | C12-lactylate plus polylysine 0.009%/0.0225% |
| *Escherichia coli* ATCC 8739 | 0.7820 | 0.7370 | 0.0027 |
| *E. coli* O157:H7 ATCC 700728 | 0.9230 | 0.6070 | 0.0000 |
| *Salmonella typhimurium* ATCC 13311 | 0.9525 | 0.9520 | 0.2663 |
| *S. enteritidis* ATCC 13076 | 0.9475 | 0.9035 | 0.0000 |

| Compound Concentration (w/w) | Observed Relative Growth Rate | | |
|---|---|---|---|
| | C14-lactylate 0.009% | polylysine 0.0225% | C14-lactylate plus polylysine 0.009%/0.0225% |
| *Escherichia coli* ATCC 8739 | 0.4750 | 0.4395 | 0.0000 |
| *E. coli* O157:H7 ATCC 700728 | 0.8850 | 0.2800 | 0.0000 |

The invention claimed is:

1. An antibacterial composition comprising a combination of
   a. a lactylate or a mixture of lactylates, represented by the following formula $(RCO-(O-CH(CH_3)-CO)_xO)_m Y(OH)_{n-m}$ wherein:
   RCO is an acyl radical of a fatty acid having 4 to 18 carbon atoms,
   Y is a cation selected from the group consisting of hydrogen, alkali metal, alkaline earth metal, zinc, iron and ammonium or substituted ammonium having one or more $C_1$-$C_3$ alkyl or hydroxy alkyl groups;
   n is a value of the cation;
   m is an integer of from 1 to n;
   x is a number of from 1 to 6; and
   x, m and n represent average numbers, and
   b. a compound selected from the group consisting of protamine, a salt of protamine, and a mixture thereof.

2. The antibacterial composition of claim 1, wherein x has a value of from 1 to 3 and the lactylate is selected from octanoyllactylate, decanoyllactylate, dodecanoyllactylate, tetradecanoyl-lactylate, oleic-lactylate, in their free form or as salt, and a mixture thereof.

3. The antibacterial composition of claim 1, the composition further comprising one or more additives selected from the group consisting of a metal chelating agent, an organic acid or a salt or ester thereof, a glycerol-based fatty acid ester and a mixture thereof.

4. The antibacterial composition of claim 1, wherein the organic acid is selected from lactic acid, acetic acid, citric acid, malic acid, fumaric acid, tartaric acid, gluconic acid, propionic acid, caproic acid and phytic acid.

5. The antibacterial composition of claim 1, wherein the glycerol-based fatty acid ester is a mono- or di-ester of glycerol or a mixture thereof.

6. The antibacterial composition of claim 1, wherein the composition is a liquid or a solid and wherein the composition comprises from 0.0001 to 40 wt % of the compound selected from the group consisting of protamine, a salt of protamine and a mixture thereof, 0.0001 to 45 wt % of the lactylate, 0 to 45 wt % of a glycerol-based fatty acid ester, 0 to 45 wt % of an organic acid or a salt or ester thereof and 0 to 98 wt % of a carrier.

7. A method for reduction or prevention of the presence, growth or activity of gram-negative bacteria into, or on, a product or surface, the method comprising applying the antibacterial composition of claim 1 into the product or the surface.

8. The method of claim 7, wherein the gram-negative bacteria is a bacterium from the family of *Escherichia coli, Salmonella, Pseudomonas* or *Campylobacter*.

* * * * *